US00PP31312P3

(12) United States Plant Patent
Hansen

(10) Patent No.: US PP31,312 P3
(45) Date of Patent: Dec. 31, 2019

(54) **X *MANGAVE* PLANT NAMED 'MAYAN QUEEN'**

(50) Latin Name: **x *Mangave* times *Agave gypsophila***
Varietal Denomination: Mayan Queen

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 91 days.

(21) Appl. No.: 15/932,527

(22) Filed: Mar. 12, 2018

(65) Prior Publication Data

US 2019/0281746 P1 Sep. 12, 2019

(51) Int. Cl.
*A01H 6/12* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 6/12; A01H 5/12
See application file for complete search history.

*Primary Examiner* — Keith O. Robinson

(57) ABSTRACT

A new and unique X *Mangave* plant named 'Mayan Queen' characterized by silver-grey, slightly-arching, slightly-wavy, lanceolate foliage with distinctly small firm spines on deeply-scalloped margins. Leaves develop greyed purple markings with strong ultraviolet light with reddish purple base. Plants are useful for landscaping as specimens or en masse or as container plants in the landscape or in the home.

1 Drawing Sheet

Botanical classification: x *Mangave* times *Agave gypsophila.*

Variety denomination: 'Mayan Queen'.

BACKGROUND OF THE INVENTION

The present invention relates to the new and distinct X *Mangave* x *Agave* hybrid plant, X *Mangave* 'Mayan Queen' hybridized by the inventor at a wholesale perennial nursery in Zeeland, Mich., USA as cross between X *Mangave* 'Bloodspot' (not patented) as the female or seed parent times an unnamed selection of *Agave gypsophila* (not patented) as the male or pollen parent. The cross was performed on Dec. 26, 2011 and seeds were harvested and later sown Aug. 8, 2012. Through trials at the same nursery the plant was originally assigned the breeder code XMANG-12-03-27. The new plant has been successfully asexually propagated initially by sterile shoot-tip tissue culture at the same nursery in Zeeland, Mich. For those skilled in the art, tissue culture methods of asexual propagation systems for 'Mayan Queen' have been found to produce stable and identical plants that maintain all the unique characteristics of the original plant.

No plants of X *Mangave* 'Mayan Queen' have been sold, under this or any name, in this country or anywhere in the world, prior to the filing of this application, except to a perennial nursery in Raleigh, N.C. No disclosure of the new plant been made prior to the filing of this application with the exception of that which was disclosed within one year of the filing of this application, and was either derived directly or indirectly from the inventor.

BRIEF SUMMARY OF THE INVENTION

X *Mangave* 'Mayan Queen' differs from its parents as well as all other *Manfreda, Agave* and X *Mangave* known to the applicant. Compared with the female parent 'Bloodspot' the new plant has broader, longer and more upright leaves with more flexible apical spines and larger, more outright, mounded habit and the spots are more uniformly distributed and more greyed-purple compared with the burgundy spots of 'Bloodspot'. Compared with the male parent, the new plant has flatter, narrower, shorter, more numerous, and less wavy foliage with more purple marking. The most similar cultivars known to the inventor are X *Mangave* 'Purple People Eater' U.S. Plant Pat. No. 29,949, X *Mangave* 'Silver Fox' U.S. Plant Pat. No. 29,642, X *Mangave* 'Mission to Mars' U.S. Plant Pat. No. 29,393 and X *Mangave* 'Lavender Lady' U.S. Plant Pat. No. 29,194. 'Purple People Eater' has shorter, less arching foliage with more intense purple marking, larger marginal and apical spines and has a more compact habit. 'Silver Fox' is more compact and has smaller foliage with more intense glaucous surfaces and less purple markings. 'Mission to Mars' has a larger habit with broader and longer foliage that is less glaucous and has intense reddish markings. 'Lavender Lady' is shorter and more compact in habit with more ovate foliage having more intense purplish markings.

The new plant, 'Mayan Queen', is unique from all of the above cultivars and all *Agave,* X *Mangave* and *Manfreda* known to the inventor by the following combined traits:

1. Slightly-arching, slightly-wavy, lanceolate foliage with distinctly small firm spines on deeply-scalloped margins;
2. Silver-grey foliage develops heavy glaucous covering and irregular greyed-purple spotting with strong ultraviolet light;
3. Dense reddish purple leaf bases and slightly-flexible apical spines;
4. Moderate growth rate.

BRIEF DESCRIPTION OF THE DRAWINGS

The photographs of x *Mangave* 'Mayan Queen'; demonstrate the overall appearance of the new plant including the unique traits of a four-year-old plant grown in a greenhouse in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
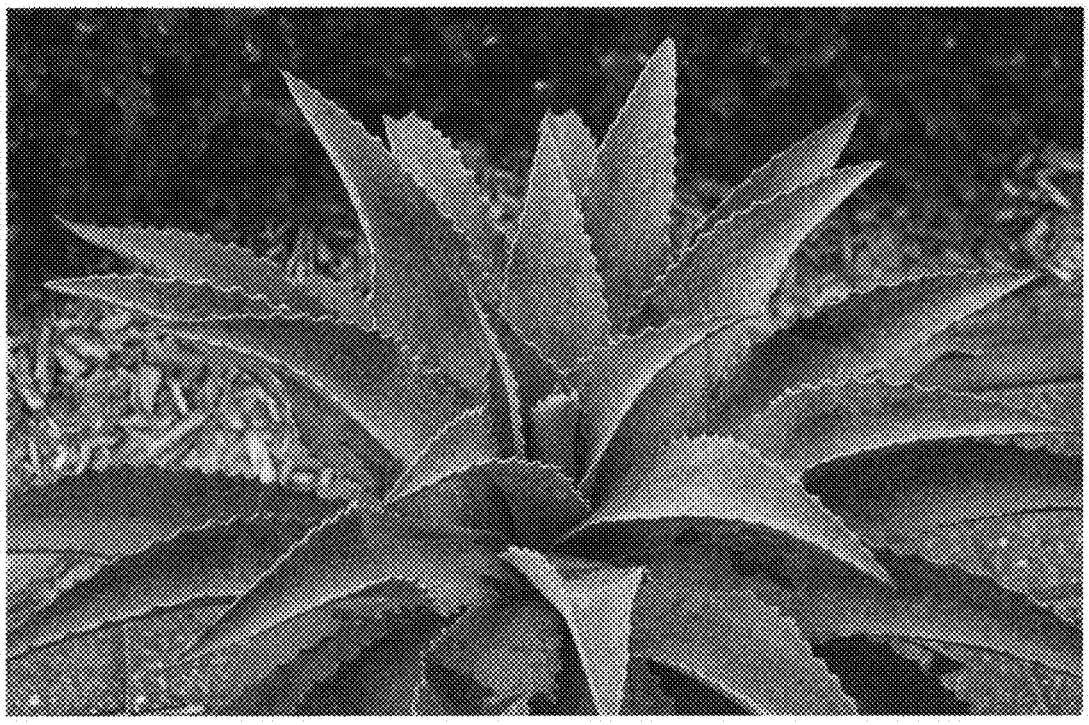
FIG. 1 shows the new plant and foliage from above.
Figure 2:
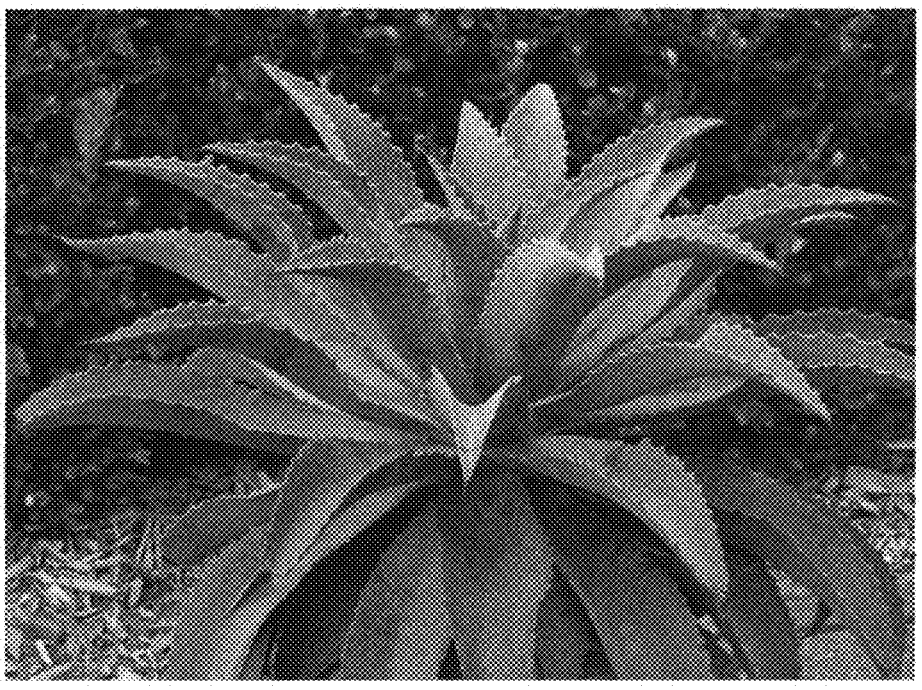
FIG. 2 shows the new plant foliage and habit from a side view.

The following descriptions and color references are based on the 2015 edition of The Royal Horticultural Society Colour Chart except where common dictionary terms are used. The new plant, X *Mangave* 'Mayan Queen', has not been observed under all possible environments. The phenotype may vary slightly with different environmental conditions, such as temperature, light, fertility, moisture and maturity levels, but without any change in the genotype. The following observations and size descriptions are of a four-year-old plant in a commercial wholesale greenhouse in Zeeland, Mich. with supplemental water and fertilizer as needed.

Parentage: X *Mangave* 'Bloodspot' as female or seed patent and an unnamed selection of *Agave gypsophila* (not patented) as the male or pollen parent;

Propagation: Division of side shoots and sterile shoot-tip tissue culture;

Time to initiate roots from tissue culture: About 21 days;

Growth rate: Moderate;

Crop time: About 12 to 16 weeks to finish in a 3.8 liter container from a 35 mm tissue culture growing at about 21° C.;

Rooting habit: Fleshy, lightly branching, with roots up to 20 cm long;

Root color: Nearest RHS 158D;

Plant shape and habit: Succulent, herbaceous, freeze-tender perennial with basal rosettes of about 40 leaves radially emerging and outwardly and slightly arching from central stem extending below the base of the plant when grown in containers, producing a radially-symmetrical, slightly outwardly mound;

Plant size: Foliage height about 28.0 cm tall from soil line to the top of the leaves and about 58.0 cm wide at the widest point slightly below soil line in container;

Foliage description: Lanceolate; simple; margins scalloped with small firm teeth; apex spinose; base truncate, sessile, clasping; flat; bi-laterally symmetrical; slightly involute to slightly conduplicate;

Leaf size: To about 30.0 cm long, about 7.5 cm wide at base and 5.0 mm thick, average about 28.5 cm long, 6.5 cm wide and 4.5 mm thick; marginal teeth about 1.0 mm long on scalloped indentations about 5.0 mm deep and about 7.5 mm apart; spots average about 3.0 mm across and may connect with intense ultraviolet light;

Foliage fragrance: None observed;

Leaf blade color:

*Adaxial* (*young*).—Nearest RHS N138B and with glaucous surface of nearest RHS 188B and spots nearest RHS N187A with intense ultraviolet light.

*Abaxial* (*young*).—Nearest RHS N138B and with glaucous surface of RHS 188B and spots nearest RHS N187B with intense ultraviolet light.

*Adaxial* (*mature*).—Nearest RHS N138D with blush of nearest RHS 188B and spots between RHS N187A and RHS N187B.

*Abaxial* (*mature*).—Nearest RHS N138D.

*Teeth.*—Nearest RHS 160B on young leaves and maturing to nearest RHS 166A.

Apical spine or mucro: Sharp and flexible; average about 4.0 mm long and about 1.0 mm wide at base;

Apical spine or mucro color: Nearest RHS 175B on young expanding leaves and maturing to nearest RHS 200B;

Petiole: Sessile;

Veins: Parallel; not distinct abaxial or adaxial;

Stem: Terete; covered with leaves; about 3.0 cm across and extending to about 4.0 cm above soil; without branching; attitude upwards, erect; Flowers have not yet been observed. Fruit and seed have not yet been observed.

Disease resistance: X *Mangave* 'Mayan Queen' has not been observed to be resistant to diseases beyond that which is normal for X *Mangave, Agave* or *Manfreda.* The plant is xeromorphic and survives well with minimal water once established. The new plant is hardy at least from USDA zone 9a to 11. Full extent of winter hardiness has not been tested.

It is claimed:

1. A new and distinct cultivar of ornamental X *Mangave* plant named 'Mayan Queen' as herein described and illustrated, suitable for the garden or as a potted plant in the garden or home.

* * * * *